(12) United States Patent
Ptchelintsev et al.

(10) Patent No.: US 8,128,914 B2
(45) Date of Patent: Mar. 6, 2012

(54) TOPICAL COMPOSITIONS CONTAINING CIS-6-NONENOL AND ITS DERIVATIVES AND METHODS FOR TREATING SKIN

(75) Inventors: Dmitri S. Ptchelintsev, Jersey City, NJ (US); Cheng Shine Hwang, New Milford, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 13/165,876

(22) Filed: Jun. 22, 2011

(65) Prior Publication Data

US 2011/0251291 A1     Oct. 13, 2011

Related U.S. Application Data

(62) Division of application No. 12/342,197, filed on Dec. 23, 2008, now Pat. No. 7,993,629.

(51) Int. Cl.
*A61K 8/34* (2006.01)
*A61Q 19/08* (2006.01)

(52) U.S. Cl. .......................................... 424/59; 514/739

(58) Field of Classification Search ........................ None
See application file for complete search history.

(56) References Cited

U.S. PATENT DOCUMENTS

| 5,582,817 A | 12/1996 | Otsu et al. |
| 2006/0153782 A1 | 7/2006 | Kelly et al. |
| 2007/0071780 A1 | 3/2007 | Dubois et al. |
| 2008/0119433 A1 | 5/2008 | Tabor |
| 2008/0221003 A1 | 9/2008 | Meine et al. |
| 2008/0292651 A1 | 11/2008 | Zimmerman et al. |

FOREIGN PATENT DOCUMENTS

| EP | 1145707 A1 | 10/2001 |
| JP | 2000-97291 A | 10/2000 |
| WO | 01/28327 A1 | 4/2001 |
| WO | 01/94438 A1 | 12/2001 |
| WO | 2004/086866 A1 | 10/2004 |

*Primary Examiner* — Tracy Vivlemore
*Assistant Examiner* — Jennifer Berrios
(74) *Attorney, Agent, or Firm* — Charles J. Zeller; Joan M. McGillycuddy

(57) ABSTRACT

Cosmetic compositions comprising cis-6-nonenol and methods of using such compositions to impart anti-aging benefits to the skin are disclosed. Cis-6-nonenol is believed to have modulatory activity against at least one biochemical pathway implicated in skin aging.

12 Claims, No Drawings

TOPICAL COMPOSITIONS CONTAINING CIS-6-NONENOL AND ITS DERIVATIVES AND METHODS FOR TREATING SKIN

CROSS-REFERENCE TO A RELATED APPLICATION

The present application is a divisional application of U.S. Ser. No. 12/342,197, filed Dec. 23, 2008, now U.S. Pat. No. 7,993,629, which are incorporated herein by reference in its entirety.

FIELD OF THE INVENTION

The present invention relates generally to compositions for topical application to the skin which comprise cis-6-nonenol and the use of such compositions to provide benefits to the skin, in particular, to provide anti-aging benefits to human skin.

BACKGROUND OF THE INVENTION

The metallothioneins are a family of cysteine-rich, low molecular weight proteins (e.g., having a molecular weight (MW) ranging from 3500 to 14000 Da). Metallothioneins have the capacity to bind both physiological (e.g., Zn, Cu, Se) and xenobiotic (e.g., Cd, Hg, Ag) heavy metals through the thiol groups of their cysteine residues, which represents nearly 30% of its amino acidic residues. Metallothionein proteins participate in the uptake, transport, and regulation of zinc in biological systems. The zinc binding sites are typically cysteine-rich, and often bind three or four zinc ions. In some metallothioneins, histidine residues also participate in zinc binding and in the determination of the metal/binding preferences. By binding and releasing zinc, metallothioneins regulate zinc levels within the body. Metallothioneins carry zinc ions from one part of a cell to another. In this way, the metallothioneins become key components of the zinc signaling system in cells. This system is particularly important in the brain, where zinc signaling is prominent both between and within nerve cells. It is also believed to be important for the regulation of the tumor suppressor protein p53.

Cysteine residues from metallothioneins can capture harmful oxidant radicals such as hydroxide radicals. From this reaction, cysteine is oxidized to cystine, and the metal ions bound to cysteine are liberated to the media. Zn released in this way can activate the more metallothioneins. This mechanism has been proposed to be an important mechanism in the control of the oxidative stress by metallothioneins.

The effect of ultraviolet radiation on metallothionein activity has been reported in several ways. Yamada et al. reported that three different cultured human skin-derived cell lines irradiated with monochromatic ultraviolet (UV) rays at 280 nm exhibited inhibition in the synthesis of synthesis of metallothioneins when induced by Cadmium, Zinc or dexamethoasone. (see Yamada, H., Murata, M. Suzuki, K., Koizumi, S., Ultraviolet irradiation increases the sensitivity of cultured human skin cells to cadmium probably through the inhibition of metallothionein gene expression, Toxicol. Appl. Pharmacol. 200: 251-257 (2004)). It has also been reported that metallothionein-null mice exhibit reduced tolerance to UVB injury.

U.S. Patent Application Publication 2007/0071780 to Dubois et al. ("Dubois") describes a personal care composition comprising a "perfume booster accord," which is said to be a perfume composition that comprises at least two high odor value materials, which improve the perceived odor intensity of a traditional fragrance. Cis-6-nonenol is listed as a suitable material for inclusion in the perfume booster accord. There is no disclosure of the anti-aging benefits of cis-6-nonenol.

PCT Patent Application Publication WO2004/86866 to Cawdell et al. ("Cawdell") describes a system for controlling insects, which system includes a substrate in the form of an elongate tape having thereon a plurality of target zones spaced apart at predetermined intervals along a first surface of the substrate, each target zone including an insect attractant and/or an insect control agent. Cawdell states that typically, in one embodiment, the interval along the continuous tape between each target zone is coated with an adhesive material. The adhesive material is said to be used to aid the attachment of the product to a crop. Alternatively, the interval along the continuous tape between each target zone is said to be of an abrasive material or a material which promotes friction between the tape and the crop. Cawdell lists numerous examples of attractants including Z-6-nonenol and E-6-nonenol.

PCT Patent Application Publication WO2001/94438 to Zander et al. ("Zander") describes urethane compounds which release organoleptically active aromatic alcohols, a method for producing said urethane compounds, and use thereof in cosmetic, glue, paint and plastic compositions, and cleaning product, softener, washing-up and dishwasher detergent compositions. Zander describes one embodiment where the urethane compounds have the formula $R[-NH-C(=O)-OR']_n$, where n=1, 2, 3 and R is derived from aliphatic, alicyclic or aromatic mono-, di-, or tri-isocyanates with 1 to 30 carbon atoms. Zander states that R' is derived from an alcohol having the formula R'OH, which may be selected from a group consisting of numerous alcohols including cis-6-nonenol, 5-ethyl-2-nonanol, 6,8-dimethyl-2-nonanol, and 2,2,8-Trimethyl-7(8)-nonen-3-ol.

PCT Patent Application Publication WO2001/28327 to Light et al. ("Light") describes bisexual attractants for lepidopterous insect pests isolated from pears or apples, a method for monitoring and control of codling moth and other species of *Lepidoptera* comprising a lure and kill, mating disruption or mass trapping strategy, and a method of using a formulation containing the bisexual attractants with or without an insecticide and/or pheromone for control of the insect pests. Light states that the attractants will preferably have the formulae:

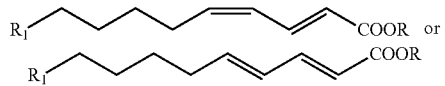

where R and $R_1$ are $-CH_3$, $-CH_2CH_3$ or $CH_2CH_2CH_3$. Light also lists numerous examples of pheromones including (Z)-6-nonenol and (E)-6-nonenol.

Japanese Patent Application Publication JP2002-97291 to Ouchi et al. ("Ouchi") describes a fragrant ingredient from a melon capillary root produced by the transduction of a microorganism gene into melon tissue. The fragrant ingredient is said to be obtained by the transduction of the microorganism gene into melon tissue to induce the capillary root and by culturing the induced melon capillary root to produce the fragrant ingredient itself. Ouchi reports that the fragrant ingredient may include 1-nonanal, 6Z-nonenol and nonadienal.

It is therefore an object of the invention to provide new compositions and methods for stimulating metallothionein production. It is a further object of the invention to improve the overall appearance of skin, including treating, reversing, and/or preventing signs of aging, such as skin wrinkles, by stimulating metallothionein production with cosmetic compositions comprising effective amounts of cis-6-nonenol.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that cis-6-nonenol is a stimulator of metallothioneins and thus is a beneficial agent against various signs of intrinsic aging and photo-aging skin.

In one aspect of the invention, cosmetic compositions are provided for improving the aesthetic appearance of skin comprising, in a cosmetically acceptable vehicle, an effective amount of cis-6-nonenol having the structure of formula I:

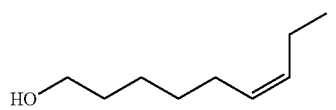

(I)

In another aspect of the invention, cosmetic compositions are provided for topical application. The cosmetic compositions comprise an effective amount of cis-6-nonenol to treat, reverse, ameliorate and/or prevent signs of skin aging. Such signs of skin aging include without limitation, the following:
(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization and/or hydration;
(o) improvement of (e.g., increase in and/or prevention of loss of) skin elasticity and/or resiliency;
(p) treatment, reduction, and/or prevention of skin sagging; and/or
(q) treatment, reduction, and/or prevention of discoloration of skin.

Also provided is a method of treating one or more signs of skin aging comprising topically applying to skin in need thereof cis-6-nonenol in an amount effective to enhance metallothioneins.

In another aspect of the invention, a method of treating, reversing, ameliorating and/or preventing fine lines or wrinkles or sagging in human skin is provided, comprising topically applying to skin in need thereof, including applying directly to a wrinkle or fine line, a composition comprising cis-6-nonenol in an amount effective to enhance metallothioneins.

These and other aspects of the present invention will be better understood by reference to the following detailed description.

DETAILED DESCRIPTION

All terms used herein are intended to have their ordinary meaning unless otherwise provided.

As used herein, "% by weight" or "% wt" refers to the weight percent of a component in relation to the total weight of the composition (i.e., including any carriers, vehicles, solvents, emollients, fillers, or other components added before application to the skin) unless otherwise specified.

The present invention provides compositions for topical application which comprise an effective amount of cis-6-nonenol to treat, reverse, ameliorate and/or prevent signs of skin aging. Such signs of skin aging include without limitation, the following:
(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization and/or hydration;
(o) improvement of (e.g., increase in and/or prevention of loss of) skin elasticity and/or resiliency;
(p) treatment, reduction, and/or prevention of skin sagging; and/or
(q) treatment, reduction, and/or prevention of discoloration of skin.

In practice, the compositions of the invention are applied to skin in need of treatment. That is, skin which suffers from a deficiency or loss in any of the foregoing attributes or which would otherwise benefit from improvement in any of the foregoing skin attributes.

The term "wrinkle" or "wrinkling" refers to both fine wrinkling and coarse wrinkling. Fine wrinkling or fine lines refers to superficial lines and wrinkles on the skin surface. Coarse wrinkling refers to deep furrows, particularly deep lines/wrinkles on the face and around the eyes, including of expression lines such as frown lines and wrinkles, forehead lines and wrinkles, crow's feet lines and wrinkles, nasolabial fold and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth. Wrinkles can be assessed for number, length, and depth of the lines.

Elasticity of the skin refers to the springiness and resilience of skin's ability to regain its original shape and size after deformation. Elasticity of the skin may be evaluated by a pinch test that can either cause deformation by stretching or squeezing the skin.

Discoloration of skin includes discrete pigmentation, which is commonly known as pigment spots or "age spots," and mottled pigmentation. Discrete pigmentation are distinct uniform areas of darker pigment and may appear as brown spots or freckles on the skin. Mottled pigmentation are dark blotches that are larger and more irregular in size and shape than discrete pigmentation. Areas of mottled pigmentation tend to become darker with sun exposure.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

The cosmetic compositions for treating a skin condition associated with intrinsic aging or skin photo-aging comprise, in a cosmetically acceptable vehicle, an amount of cis-6-nonenol, having the structure of formula (I):

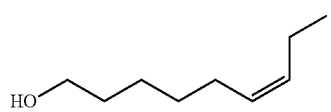

(I)

The composition are believed to be effective to enhance metallothionein activity, which is expected to increase the photoprotective properties of the skin, as it has surprisingly been discovered through exploratory biopsies that metallothioneins are down-regulated in UV exposed skin (e.g., 53% in 18-25 year old skin and 85% in 41-67 year old skin).

The compositions according to the invention can be formulated in a variety of forms for topical application and will comprise from about 0.0001% to about 90% by weight of cis-6-nonenol, and preferably will comprise from about 0.001% to about 25% by weight, and more preferably from about 0.01% to about 10% by weight. Within the more preferred range, the composition may comprise cis-6-nonenol within a range from about 0.1%, 0.25%, 0.5%, 0.75% or about 1% up to about 5%, 7.5% or about 10% by weight of the total composition. The compositions will comprise an effective amount of cis-6-nonenol, by which is meant an amount sufficient to stimulate production of metallothionein in given area of skin when topically applied thereto.

In one embodiment, the composition is essentially free of the trans-6-nonenol isomer or essentially free of nonenol isomers having the double bond in positions other than the 6-position. By "essentially free of" is meant that such other nonenol constituents will comprise less than 5% by weight of the total amount of nonenol, preferably, less than 2.5% by weight, and more preferably, less than 1% by weight. In other embodiments, the compositions will be free of nonenols other than cis-6-nonenol.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle. Such vehicles may take the form of any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8\text{-}20}$ isoparaffins. Paraffinic hydrocarbons are available from Exxon under the ISOPARS trademark, and from the Permethyl Corporation. In addition, $C_{8\text{-}20}$ paraffinic hydrocarbons such as $C_{12}$ isoparaffin (isododecane) manufactured by the Permethyl Corporation having the tradename Permethyl 99ATM are also contemplated to be suitable. Various commercially available $C_{16}$ isoparaffins, such as isohexadecane (having the tradename Permethyl®) are also suitable.

Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The preferred emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: sorbitan esters; polyglyceryl-3-diisostearate; $C_{10-30}$ alkyl acrylate crosspolymer; Dimethicone PEG-7 isostearate, acrylamide copolymer; mineral oil; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, from about 0.1% to about 3% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -$(EO)_m$— and/or —(PO)— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SI LWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

In certain embodiments, the composition may comprise up to about 70% by weight of volatile solvent(s), including volatile organic solvents. Specifically, the composition may comprise up to about 60%, preferably up to about 50%, more preferably up to about 40%, and even more preferably up to about 30% by weight of volatile solvent(s). In other embodiments, the composition may be free of volatile solvents, including volatile organic solvents.

The compositions may include liposomes. The liposomes may comprise other additives or substances and/or may be modified to more specifically reach or remain at a site following administration.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions of the invention may include a fragrance. Fragrances are substances which can impart an aesthetically pleasing aroma to the composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the composition in an amount ranging from about 0.001 to about 5 weight percent, preferably about 0.01 to about 0.5 percent by weight. In other embodiments, the compositions of the invention will be fragrance-free, by which is meant that the composition will not contain fragrances, in particular components that are added for the primary benefit of providing aroma.

The present compositions may also contain one or more insect repellent actives. Such actives include, but are not limited to, N,N diethyl-m-toluamide (DEET), ethyl butylacetylaminopropionate (IR3535 by Merck Co.), hydroxyethyl isobutyl piperidine carboxylate (1-piperidine carboxylic acid) (Bayer KBR 3023), p-menthane-3,8-diol, oil of citronella, soy bean oil, lemon grass oil, geranium/geraniol oil, neem oil and other natural essential oils, p-menthane-3,8-diol, or any mixtures thereof. The insect repellent active may be present in an amount about 0.05 wt % to about 90 wt %, preferably about 0.1 wt % to about 50 wt %, and most preferably about 0.1 wt % to about 30 wt %, based on the total weight of the composition. In other embodiments, the compositions of the invention will be free of an insect repellent active, by which is meant that the composition will not contain insect repellents, e.g., components that are typically added for the primary benefit of repelling insects.

In one embodiment of the invention, the compositions may include additional skin actives such as, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, advanced glycation end-product (AGE) inhibitors and alpha-hydroxyacids.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Anogeissus latifolia, Asmunda japonica, Azadirachta indica, Butea frondosa, Butea monospenna, Cedrus deodara, Emblica officinalis, Ficus benghalensis, Glycyrrhiza glabra, Ilex purpurea Hassk, Innula racemosa, Ligusticum chiangxiong, Ligusticum lucidum, Mallotus philippinensis, Mimusops elengi, Morinda Moringa oleifera, Naringi crenulata, Nerium indicum, Psoralea corylifolia, Stenoloma chusana, Terminalia bellerica*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alphahydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is preferred that the composition be essentially free of components having a strong oxidizing potential, including for example, organic or inorganic peroxides. By "essentially free of" these components is meant that the amounts present are insufficient to have a measurable impact on the metallothionein enhancing activity of cis-6-nonenol. In some embodiments, this will be, on a molar basis in relation to the amount of cis-6-nonenol, less than 1%.

In one embodiment, the composition of the invention comprising cis-6-nonenol may have a pH between about 1 and about 8. In certain embodiments, the pH of the composition will be acidic, i.e., less than 7.0, and preferably will be between about 2 and about 7, more preferably between about 3.5 and about 5.5.

The invention provides a method for treating aging skin by topically applying a composition comprising cis-6-nonenol, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging. Specifically, this method is contemplated to be useful for treatment of UV damaged skin.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration;

improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

Without wishing to be bound by any particular theory, it is believed that the compositions of the present invention enhance and improve the aesthetic appearance of skin by stimulation of metallothionein.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

The cis-6-nonenol active component is topically applied to an "individual in need thereof," by which is meant an individual that stands to benefits from reducing visible signs of skin damage or aging. In a specific embodiment, the cis-6-nonenol component is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive cis-6-nonenol compositions to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of aging skin, including wrinkles, on the skin of the hands, arms, legs, neck, chest, and face, including the forehead.

It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

EXAMPLES

Example 1

Stimulation of Metallothioneins

Normal human dermal fibroblasts were cultured in 96 well tissue culture treated plates, containing appropriate culture medium. Stock solution of cis-6 nonenol was made in ethanol. Cells were treated with test material or ethanol vehicle control diluted in growth medium for 24 hours in a humidified 37° C. incubator with 10% $CO_2$. After incubation, growth medium from each plate was removed and 100 μl of lysis buffer was added to the wells and placed in 37° C. incubator with 10% $CO_2$ for 30 minutes. At the end of incubation, the cells were collected in freezer plates and placed in −80° C. freezer, until analysis. Changes in mRNA for Metallothionein 2A (MT2A) after treatment were analysed using Panomics' QuantiGene® multiplex assay that employs a branched DNA technology. Percent increase in mRNA for MT2A was calculated by comparing the test results to that of the vehicle control. Fibroblasts treated with 0.01% or 0.001% of Cis-6-nonenol showed a 96% and 97% stimulation in mRNA levels for Metallothionein 2A, respectively. All results reported are statistically significant at $p<0.05$.

Example 2

Exemplary Compositions

Cosmetic compositions comprising cis-6-nonenol for topical application to the skin are provided in Table 1.

TABLE 1

| Components | Composition: 1 Weight % | 2 | 3 | 4 |
|---|---|---|---|---|
| cis-6-nonenol | 0.5 | 0.05 | 0.01 | 0.005 |
| Acrylates/C10-30 Alkyl Acrylate Crosspolymer | 1 | 1 | 1 | 1 |
| Cetyl Ethylhexanoate | 10 | 10 | 10 | 10 |
| C12-15 Alkyl Benzoate | 3.9 | 3.9 | 3.9 | 3.9 |
| Isopropyl Isostearate | 3 | 3 | 3 | 3 |
| Diisopropyl dimer dillinoleate | 0.1 | 0.1 | 0.1 | 0.1 |
| Tocopheryl acetate | 0.5 | 0.5 | 0.5 | 0.5 |
| Butylene glycol | 2 | 2 | 2 | 2 |
| Propylene glycol | 1 | 1 | 1 | 1 |
| Dimethicone PEG-7 isostearate | 0.5 | 0.5 | 0.5 | 0.5 |
| Methyl gluceth-20 | 0.5 | 0.5 | 0.5 | 0.5 |
| Triethanolamine | 1 | 1 | 1 | 1 |
| Acrylates/acrylamide copolymer/mineral oil | 1.5 | 1.5 | 1.5 | 1.5 |
| DMDM Hydantoin/ Iodopropynylbutylcarbonate | 0.4 | 0.4 | 0.4 | 0.4 |
| Deionized water | q.s. | q.s. | q.s. | q.s. |
| Total: | 100 | 100 | 100 | 100 |

These compositions are believed to be effective to treat, reverse, ameliorate and/or prevent signs of skin aging, specifically, the compositions are believed to reduce the appearance of fine lines and wrinkles in the skin. The compositions of Table 1 are applied to skin in need of treatment, by which is meant skin in need of an anti-aging benefit, and in particular skin having wrinkles and/or fine lines. The cosmetic compositions may be applied directly to the fine lines and/or wrinkles. The exemplary compositions may be applied to treat, reverse, ameliorate and/or prevent fine lines and/or wrinkles on any surface of the skin, including without limitation, the skin of the face, neck, and/or hands.

The cosmetic compositions are applied to the skin, fine line and/or wrinkle one, two or three times daily for as long as is necessary to achieve desired anti-aging results, which treatment regiment may comprise daily application for at least one week, at least two weeks, at least four weeks, at least eight weeks, or at least twelve weeks. Alternatively, the exemplary cosmetic compositions may be used in chronic treatment of the skin, fine line and/or wrinkle.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for imparting an anti-aging benefit to human skin comprising: topically applying to the skin of an individual in need thereof a composition in a cosmetically acceptable vehicle comprising an amount of cis-6-nonenol, in isolated or purified form, from 0.0001 weight % to 90 weight % based on the total weight of the composition effective to impart the anti-aging benefit to the skin.

2. The method according to claim 1, wherein the skin suffers from skin photo-aging.

3. The method according to claim 1, wherein said anti-aging benefit is selected from the group consisting of:
   (a) treatment, reduction, and/or prevention of fine lines or wrinkles,
   (b) reduction of skin pore size,
   (c) improvement in skin thickness, plumpness, and/or tautness;
   (d) improvement in skin suppleness and/or softness;
   (e) improvement in skin tone, radiance, and/or clarity;
   (f) improvement in procollagen and/or collagen production;
   (g) improvement in maintenance and remodeling of elastin;
   (h) improvement in skin texture and/or promotion of retexturization;
   (i) improvement in skin barrier repair and/or function;
   (j) improvement in appearance of skin contours;
   (k) restoration of skin luster and/or brightness;
   (l) replenishment of essential nutrients and/or constituents in the skin;
   (m) improvement of skin appearance decreased by menopause;
   (n) improvement in skin moisturization;
   (o) improvement of skin elasticity and/or resiliency; or
   (p) treatment, reduction, and/or prevention of skin sagging; and/or
   (q) treatment, reduction, and/or prevention of discoloration of skin.

4. The method according to claim 3, wherein said anti-aging benefit is the treatment, reduction, and/or prevention of fine lines or wrinkles.

5. The method according to claim 3, wherein said anti-aging benefit is the treatment, reduction, and/or prevention of skin sagging.

6. The method according to claim 3, wherein said anti-aging benefit is treatment, reduction, and/or prevention of discoloration of skin.

7. The method according to claim 3, wherein said anti-aging benefit is improvement of skin elasticity.

8. The method according to claim 1, wherein said cis-6-nonenol is present in an amount sufficient to enhance metallothionein activity.

9. The method according to claim 1, wherein the cis-6-nonenol is present in an amount from 0.001 weight % to 25 weight % based on the total weight of the composition.

10. The method according to claim 9, wherein said cis-6-nonenol is present in an amount from 0.01 weight % to 10 weight % based on the total weight of the composition.

11. A method for treating wrinkles and/or fine lines comprising: topically applying to said wrinkle and/or fine line on the skin of an individual in need thereof a composition in a cosmetically acceptable vehicle comprising an amount of cis-6-nonenol, in isolated or purified form, from 0.0001 weight % to 90 weight % based on the total weight of the composition for a time sufficient to reduce the severity of said wrinkles or fine lines.

12. A method for providing a benefit to human skin comprising: topically applying to an area of the skin damaged by UV radiation a composition in a cosmetically acceptable vehicle comprising an amount of cis-6-nonenol, in isolated or purified form, from 0.0001 weight % to 90 weight % based on the total weight of the composition for a time sufficient to improve the aesthetic appearance of the skin.

* * * * *